(12) United States Patent
Hakuta et al.

(10) Patent No.: US 8,461,340 B2
(45) Date of Patent: Jun. 11, 2013

(54) METHOD FOR PRODUCING CIS-3-SUBSTITUTED-3-AZABICYCLO[3.2.1]OCTAN-8-OL DERIVATIVE

(75) Inventors: Hiroshi Hakuta, Takaoka (JP); Tsutomu Imagawa, Takaoka (JP); Hirohito Oooka, Hadano (JP); Shinya Fukuhara, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 343 days.

(21) Appl. No.: 12/674,326

(22) PCT Filed: Aug. 27, 2008

(86) PCT No.: PCT/JP2008/065318
§ 371 (c)(1),
(2), (4) Date: Feb. 19, 2010

(87) PCT Pub. No.: WO2009/028563
PCT Pub. Date: Mar. 5, 2009

(65) Prior Publication Data
US 2010/0286398 A1    Nov. 11, 2010

(30) Foreign Application Priority Data
Aug. 30, 2007 (JP) ................................. 2007-223777

(51) Int. Cl.
*C07D 221/22* (2006.01)
(52) U.S. Cl.
USPC ....................................................... 546/183
(58) Field of Classification Search
None
See application file for complete search history.

(56) References Cited

FOREIGN PATENT DOCUMENTS
WO    WO 2008/044702 A1    4/2008

OTHER PUBLICATIONS

Ungnade, H. E. "The Isomers of 4-Phenyl- and 4-Cyclohexyl-cyclohexanol." J. Org. Chem. 1948, 13, 361-370.*

Nishide, K. "Recent Development of Asymmetric Syntheses Based on the Meerwein-Ponndorf-Verley Reduction." Chirality 2002, 14, 759-767.*

Cha, J. S. "Recent Developments in Meerwein-Ponndorf-Verley and Related Reactions for the Reduction of Organic Functional Groups Using Aluminum, Boron, and Other Metal Reagents: A Review." Org. Proc. Res. Dev. 2006, 10, 1032-1053.*

House et al., "Reduction of Azabicyclic Ketones," *Journal of Organic Chemistry*, 1963, vol. 28, pp. 2407-2416.

Balasubramanian et al., "Studies of Conformation-1, Preparation and Stereochemistry of Some 4-Piperidinols," *Tetrahedron*, 1963, vol. 19, pp. 2135-2143, Pergamon Press Ltd, Northern Ireland.

Radhakrishnan et al., "Preparation & Stereochemsitry of Some Substituted Piperdines," *Indian Journal of Chemistry*, Apr. 1973, vol. 11, pp. 318-320.

Bakvall, "Transition metal hydrides as active intermediates in hydrogen transfer reactions," *Journal of Organometallic Chemsitry*, 2002, vol. 652, pp. 105-111, Elsevier Science B.V.

Ogura, "Kagakusha no Tame no Kiso Koza Yuki Jinmei Hanno," 1998, pp. 56-57.

Kim et al., "Synthesis and Pharmacology of Site Specific Cocaine Abuse Treatment Agents: 8-Substituted Isotropane (3-Azabicyclo[3.2.1]octane) Dopamine Uptake," *J. Med. Chem.*, vol. 46, pp. 1456-1464, 2003, American Chemical Society.

Ito et al., "Rapid racemization of chiral non-racemic sec-alcohols catalyzed by ($\eta^5$-$C_5(CH_3)_5$)Ru complexes bearing tertiary phosphine-primary amine chelate ligands," *Tetrahedron Letters*, vol. 44, pp. 7521-7523, 2003, Elsevier Ltd.

International Search Report issued on Nov. 18, 2008 in International Application No. PCT/JP2008/065318 (with translation).

* cited by examiner

*Primary Examiner* — Joseph K. McKane
*Assistant Examiner* — Amanda L. Aguirre
(74) *Attorney, Agent, or Firm* — Foley & Lardner LLP

(57) ABSTRACT

There are provided, according to the present invention, a method for producing a cis-3-substituted-3-azabicyclo[3.2.1]octan-8-ol derivative, the method characterized in that a trans-3-substituted-3-azabicyclo[3.2.1]octan-8-ol derivative or a mixture of the trans- and cis-3-substituted-3-azabicyclo[3.2.1]octan-8-ol derivatives is isomerized in the presence of an aluminum compound represented by a formula $Al(OR^1)_3$ (wherein $R^1$ represents a hydrocarbon group in which a carbon atom having an oxygen atom bonded thereto is a secondary carbon atom). In the process, a ketone compound may be further added, in addition to the aluminum compound.

11 Claims, No Drawings

METHOD FOR PRODUCING CIS-3-SUBSTITUTED-3-AZABICYCLO[3.2.1]OCTAN-8-OL DERIVATIVE

TECHNICAL FIELD

The present invention relates to a novel method for producing a cis-3-substituted-3-azabicyclo[3.2.1]octan-8-ol derivative which is a useful intermediate for agricultural chemicals or pharmaceutical products.

Priority is claimed on Japanese Patent Application No. 2007-223777, filed Aug. 30, 2007, the content of which is incorporated herein by reference.

BACKGROUND ART

As a method for producing a cis-3-substituted-3-azabicyclo[3.2.1]octan-8-ol derivative, for example, a method in which 3-methyl-3-azabicyclo[3.2.1]octan-8-one is reduced with metallic sodium, and is then heated for 230 hours in the presence of benzophenone is known (refer to Non-Patent Document 1).

In addition, a method is known in which 3-methyl-3-azabicyclo[3.2.1]octan-8-one is reduced by a routine procedure to obtain the trans form thereof, and is then converted into triflate, followed by the inversion thereof with an acid (refer to Non-Patent Document 2).

Meanwhile, a racemization reaction of optically active alcohols using a ruthenium complex as a catalyst is known (refer to Non-Patent Documents 3 and 4).

[Non-Patent Document 1] J. Org. Chem., 1963, 28, 2407
[Non-Patent Document 2] J. Med. Chem., 2003, 46, 1456
[Non-Patent Document 3] J. Organomet., Chem., 2002, 652, 105
[Non-Patent Document 4] Tetrahedron Lett., 2003, 44, 7521

DISCLOSURE OF INVENTION

Problems to be Solved by the Invention

However, the method described in Non-Patent Document 1 has problems that reaction time is long, and moreover, the yield of the target cis form is low. In the method of Non-Patent Document 2, there are problems as an industrial production method because the reaction has to undergo multiple stages and trifluoromethanesulfonic acid anhydride used as a reagent is expensive. On the other hand, an example in which a hydrogen transfer reaction using a transition metal complex is applied for a racemization reaction has been conventionally known. However, in the case of racemization, since the inversion process advances only up to 50% at a maximum, it has been considered that a preferential inversion from one isomer to another isomer is not possible.

An object of the present invention is to provide a method for producing a cis-3-substituted-3-azabicyclo[3.2.1]octan-8-ol derivative which is industrially useful, with a high yield and versatility.

Means for Solving the Problems

In order to solve the above-mentioned problems, the present inventors have conducted intensive and extensive studies, and as a result, they have discovered that a cis form of a 3-substituted-3-azabicyclo[3.2.1]octan-8-ol derivative can be obtained at a high yield by isomerizing either a trans form of the 3-substituted-3-azabicyclo[3.2.1]octan-8-ol derivative or a mixture of the trans form and cis form thereof, in the presence of trialkoxyaluminum having alkoxy groups formed of alicyclic hydrocarbonoxy groups in which the carbon atom having an oxygen atom bonded thereto is a secondary carbon atom. Based on this, the present invention has been completed.

That is, the present invention relates to the followings.

(1) A method for producing a cis-3-substituted-3-azabicyclo[3.2.1]octan-8-ol derivative, the method characterized in that either a trans-3-substituted-3-azabicyclo[3.2.1]octan-8-ol derivative or a mixture of the trans- and cis-3-substituted-3-azabicyclo[3.2.1]octan-8-ol derivatives is isomerized, in the presence of an aluminum compound represented by a formula $Al(OR^1)_3$ (in the formula, $R^1$ represents a hydrocarbon group in which a carbon atom having an oxygen atom bonded thereto is a secondary carbon atom).

(2) The method for producing a cis-3-substituted-3-azabicyclo[3.2.1]octan-8-ol derivative according to the above aspect (1), characterized in that an $R^1$ group in the formula $Al(OR^1)_3$ is an alicyclic hydrocarbon group.

(3) The method for producing a cis-3-substituted-3-azabicyclo[3.2.1]octan-8-ol derivative according to the above aspect (2), characterized in that the alicyclic hydrocarbon group is an alicyclic hydrocarbon group having a 6-membered ring structure.

(4) The method for producing a cis-3-substituted-3-azabicyclo[3.2.1]octan-8-ol derivative according to the above aspect (1), characterized by further conducting an isomerization in the presence of a ketone compound.

(5) The method for producing a cis-3-substituted-3-azabicyclo[3.2.1]octan-8-ol derivative according to the above aspect (4), characterized in that the ketone compound is an alicyclic ketone compound.

(6) The method for producing a cis-3-substituted-3-azabicyclo[3.2.1]octan-8-ol derivative according to the above aspect (5), characterized in that the alicyclic ketone compound is a ketone compound having a 6-membered ring structure.

(7) The method for producing a cis-3-substituted-3-azabicyclo[3.2.1]octan-8-ol derivative according to any one of the above aspects (1) to (6), characterized in that either a trans-3-substituted-3-azabicyclo[3.2.1]octan-8-ol derivative or a mixture of the trans- and cis-3-substituted-3-azabicyclo[3.2.1]octan-8-ol derivatives is obtained by reducing a 3-substituted-3-azabicyclo[3.2.1]octan-8-one derivative.

(8) A method for producing a cis-3-substituted-3-azabicyclo[3.2.1]octan-8-ol derivative, the method characterized by including a step of conducting a reaction for reducing a 3-substituted-3-azabicyclo[3.2.1]octan-8-one derivative, in the presence of trialkoxyaluminum in which a carbon atom having an oxygen atom bonded thereto is a secondary carbon atom, thereby obtaining either a trans-3-substituted-3-azabicyclo[3.2.1]octan-8-ol derivative or a mixture of the trans- and cis-3-substituted-3-azabicyclo[3.2.1]octan-8-ol derivatives; and a step of conducting an isomerization thereof, in the presence of an aluminum compound represented by a formula $Al(OR^1)_3$ (in the formula, $R^1$ represents a hydrocarbon group in which a carbon atom having an oxygen atom bonded thereto is a secondary carbon atom).

(9) The method for producing a cis-3-substituted-3-azabicyclo[3.2.1]octan-8-ol derivative according to the above aspect (8), characterized by further including a step of conducting an isomerization in the presence of a ketone compound.

Effect of the Invention

By conducting a reaction in the presence of an aluminum compound represented by the formula $Al(OR^1)_3$ (in the formula, $R^1$ represents a hydrocarbon group in which a carbon atom having an oxygen atom bonded thereto is a secondary carbon atom), and preferably by further conducting a reaction in the presence of an alicyclic ketone compound, an isomerization from a trans-3-substituted-3-azabicyclo[3.2.1]octan-8-ol derivative to the cis form thereof can be achieved at a high yield. For this reason, it has become possible to provide a method which can be applied industrially.

BEST MODE FOR CARRYING OUT THE INVENTION

In the present invention, an isomerization reaction from a trans-3-substituted-3-azabicyclo[3.2.1]octan-8-ol derivative to a cis-3-substituted-3-azabicyclo[3.2.1]octan-8-ol derivative is conducted in the presence of an aluminum compound represented by the formula $Al(OR^1)_3$ (in the formula, $R^1$ represents a hydrocarbon group in which a carbon atom having an oxygen atom bonded thereto is a secondary carbon atom), preferably in the presence of the aforementioned aluminum compound and a ketone compound.

(3-Substituted-3-Azabicyclo[3.2.1]Octan-8-ol)

In the present description, a steric configuration of cis-3-substituted-3-azabicyclo[3.2.1]octan-8-ol derivatives is represented by the steric configuration shown in the following chemical formula (1), and a steric configuration of trans-3-substituted-3-azabicyclo[3.2.1]octan-8-ol derivatives is represented by the steric configuration shown in the following chemical formula (2). Note that the cis-3-substituted-3-azabicyclo[3.2.1]octan-8-ol derivatives are not limited to the compounds represented by the chemical formula (1), and may be a compound that further includes other substituents on the azabicyclo[3.2.1]octane ring. There are no particular limitations on the substituent, as long as it is a group which does not interfere with the isomerization reaction. However, specific examples thereof include the same groups as those mentioned as the examples of the substituent R described later.

In the formulas, there are no particular limitations on the substituent R, as long as it is a group which does not interfere with the isomerization reaction. However, more specifically, an alkyl group of 1 to 6 carbon atoms, a cycloalkyl group of 3 to 7 carbon atoms, an alkenyl group of 2 to 10 carbon atoms, a cycloalkenyl group of 4 to 10 carbon atoms, an aryl group of 6 to 10 carbon atoms, an aralkyl group of 7 to 10 carbon atoms, or a heterocyclic group formed of a 5- to 7-membered ring is preferred.

Examples of the alkyl group of 1 to 6 carbon atoms include a methyl group, an ethyl group, an n-propyl group, an isopropyl group, an n-butyl group, an s-butyl group, an isobutyl group, a t-butyl group and an n-hexyl group.

Examples of the cycloalkyl group of 3 to 7 carbon atoms include a cyclopropyl group, a cyclopentyl group, a cyclohexyl group, a cycloheptyl group, a cyclopropylmethyl group, a cyclopropylethyl group, a cyclopentylmethyl group and a cyclohexylmethyl group.

Examples of the alkenyl group of 2 to 10 carbon atoms include a vinyl group, an allyl group, a 2-propenyl group, a 2-butenyl group, a 3-butenyl group, a 2-hexenyl group and a 4-hexenyl group.

Examples of the cycloalkenyl group of 4 to 10 carbon atoms include a cyclobutenyl group, a cyclobutenylmethyl group, a cyclopentenyl group, a cyclopentenylmethyl group and a cyclohexenylmethyl group.

Examples of the aryl group of 6 to 10 carbon atoms include a phenyl group, a 1-naphtyl group and a 2-naphtyl group.

Examples of the aralkyl group of 7 to 10 carbon atoms include a benzyl group and a phenethyl group.

In addition, examples of the heterocyclic group formed of a 5- to 7-membered ring include a furan-2-yl group, a furan-3-yl group, a thiophen-2-yl group, a thiophen-3-yl group, a pyrrol-2-yl group, a pyrrol-3-yl group, an oxazol-2-yl group, an oxazol-4-yl group, an oxazol-5-yl group, a thiazol-2-yl group, a thiazol-4-yl group, a thiazol-5-yl group, an isooxazol-3-yl group, an isooxazol-4-yl group, an isooxazol-5-yl group, an isothiazol-3-yl group, an isothiazol-4-yl group, an isothiazol-5-yl group, an imidazol-2-yl group, an imidazol-4-yl group, an imidazol-5-yl group, a pyrazol-3-yl group, a pyrazol-4-yl group, a pyrazol-5-yl group, a 1,3,4-oxadiazol-2-yl group, a 1,3,4-thiadiazol-2-yl group, a 1,2,3-triazol-4-yl group, a 1,2,4-triazol-3-yl group, a 1,2,4-triazol-5-yl group, a pyridin-2-yl group, a pyridin-3-yl group, a pyridin-4-yl group, a pyridazin-3-yl group, a pyridazin-4-yl group, a pyrazin-2-yl group, a pyrimidin-2-yl group, a pyrimidin-4-yl group, a pyrimidin-5-yl group, a 1,3,5-triazin-2-yl group, a 1,2,4-triazin-3-yl group, a 2-furfurylmethyl group, a 3-thienylmethyl group, a 1-methyl-3-pyrazolomethyl group, a pyridin-2-yl group, a pyridin-3-yl group, a pyridin-4-yl group, a pyridazin-3-yl group, a pyridazin-4-yl group, a pyrazin-2-yl group, a pyrimidin-2-yl group, a pyrimidin-4-yl group, a pyrimidin-5-yl group, a 1,3,5-triazin-2-yl group, a 1,2,4-triazin-3-yl group, a 2-pyridylmethyl group, a 3-pyridylmethyl group, a 6-chlor-3-pyridylmethyl group, a 2-pyrimidylmethyl group, a tetrahydrofuran-2-yl group, a tetrahydropyran-4-yl group, a piperidin-3-yl group, a pyrrolidin-2-yl group, a morpholino group, a piperidino group, an N-methylpiperazinyl group, a 2-tetrahydrafuranylmethyl group, a 3-piperazylmethyl group, an N-methyl-3-pyrrolidylmethyl group and a morpholinomethyl group.

(Aluminum Compound)

An aluminum compound used in the present invention is represented by the formula $Al(OR^1)_3$ (in the formula, $R^1$ represents a hydrocarbon group in which a carbon atom having an oxygen atom bonded thereto is a secondary carbon atom). There are no limitations, in terms of the number of carbon atoms or the like, on the above-mentioned hydrocarbon group in which a carbon atom having an oxygen atom bonded thereto is a secondary carbon atom, as long as the aforementioned isomerization reaction is not inhibited. However, preferred examples thereof include those in which a carbon atom having an oxygen atom bonded thereto is a secondary carbon atom, such as an alkyl group of 3 to 10 carbon atoms, a cycloalkyl group of 3 to 10 carbon atoms, an alkenyl group of 2 to 10 carbon atoms, a cycloalkenyl group of 4 to 10 carbon atoms and an aralkyl group of 7 to 10 carbon atoms. Among these various possibilities, an alicyclic hydrocarbon group such as a cycloalkyl group is more preferable, and an alicyclic hydrocarbon group having a 6-membered ring structure is particularly desirable.

Examples of the alkyl group of 3 to 10 carbon atoms in which a carbon atom having an oxygen atom bonded thereto is a secondary carbon atom include an isopropyl group, an s-butyl group, an s-pentyl group, an s-heptyl group, an n-pentan-3-yl group, an n-octan-3-yl group and an n-decan-4-yl group.

Examples of the cycloalkyl group of 3 to 10 carbon atoms in which a carbon atom having an oxygen atom bonded thereto is a secondary carbon atom include a cyclopropyl group, a cyclobutyl group, a cyclopentyl group, a cyclohexyl group, a cycloheptyl group, a 2-methylcyclopropyl group, a 2-methylcyclopentyl group, a 3-methylcyclobutyl group, a 3-methylcyclopentyl group, a 4-methylcyclohexyl group, a 4-methylcycloheptyl group, a 1-methyl-1-cyclopropylmethyl group and a 1-methyl-1-cyclohexylmethyl group.

Examples of the alkenyl group of 3 to 10 carbon atoms in which a carbon atom having an oxygen atom bonded thereto is a secondary carbon atom include a 3-buten-2-yl group, a 4-penten-3-yl group, a 4-penten-2-yl group, a 5-hexen-2-yl group and a 7-octan-2-yl group.

Examples of the cycloalkenyl group of 4 to 10 carbon atoms in which a carbon atom having an oxygen atom bonded thereto is a secondary carbon atom include a 2-cyclobutenyl group, a 2-cyclopentenyl group, a 2-cyclohexenyl group, a 2-cycloheptenyl group, a 2-methyl-2-cyclobutenyl group, a 2-methyl-2-cyclopentenyl group and a 3-methyl-2-cyclohexenyl group.

Examples of the aralkyl group of 7 to 10 carbon atoms in which a carbon atom having an oxygen atom bonded thereto is a secondary carbon atom include a 1-methyl-benzyl group, a 1-ethyl-benzyl group and a 1-methyl-phenethyl group.

Within the aforementioned aluminum compound, 3 $OR^1$ groups may be the same or may be different from each other.

These aluminum compounds may be prepared in advance for use, or the aluminum compounds produced in a reaction system by replacing an alkoxy group may be used without isolation.

Specific examples of the aluminum compound used in the present invention include triisopropoxy aluminum and tricyclohexyloxy aluminum.

(Ketone Compound)

A ketone compound used in the present invention is a compound represented by a formula $R^2$—CO—$R^3$. In the formula, there are no particular limitations on $R^2$ and $R^3$ in terms of the number of carbon atoms or the like, as long as they do not interfere with the isomerization reaction. However, an alkyl group of 1 to 6 carbon atoms, a cycloalkyl group of 3 to 7 carbon atoms, an alkenyl group of 2 to 10 carbon atoms, a cycloalkenyl group of 4 to 10 carbon atoms, an aryl group of 6 to 10 carbon atoms, an aralkyl group of 7 to 10 carbon atoms, or a heterocyclic group formed of a 5- to 7-membered ring is preferred. $R^2$ and $R^3$ may be the same or may be different from each other. In addition, $R^2$ and $R^3$ may form a 5- to 10-membered ring together.

Among these various possibilities, an alicyclic ketone compound in which $R^2$ and $R^3$ are forming a 5- to 10-membered ring together is more preferable, and an alicyclic ketone compound having a 6-membered ring structure is particularly desirable.

$R^2$ and $R^3$ may include a substituent on the functional group exemplified above within a chemically acceptable range, and examples of the substituent include the same groups as those defined for the substituent R of 3-substituted-3-azabicyclo[3.2.1]octan-8-ol.

Specific examples of the ketone compound include acetone, methyl ethyl ketone, diethylketone, methyl isobutyl ketone and dipropyl ketone, and examples thereof in which $R^2$ and $R^3$ are forming a 5- to 10-membered ring together include cyclopentanone, cyclohexanone, cycloheptanone, 2-methyl-cyclopentanone, 2-cyclohexen-1-one and 3-cyclohexen-1-one.

(Production Method)

The isomerization reaction is preferably carried out, for example, by heating, under reflux and in a solvent, a trans-3-substituted-3-azabicyclo[3.2.1]octan-8-ol derivative or a mixture of the trans- and cis-3-substituted-3-azabicyclo[3.2.1]octan-8-ol derivatives, in the presence of an aluminum compound represented by the aforementioned formula $Al(OR^1)_3$ (in the formula, $R^1$ represents a hydrocarbon group in which a carbon atom having an oxygen atom bonded thereto is a secondary carbon atom), and more preferably carried out by further adding a ketone compound.

The amount of aluminum compound added is typically within a range from 10 to 200 mol % and preferably within a range from 30 to 100 mol %, with respect to 1 mole of a raw material compound. In addition, the amount of ketone compound added is typically within a range from 10 to 500 mol % and preferably within a range from 90 to 300 mol %, with respect to 1 mole of a raw material compound. The isomerization reaction is typically conducted at a temperature within a range from room temperature to reflux temperature.

There are no particular limitations on the method by which a trans-3-substituted-3-azabicyclo[3.2.1]octan-8-ol derivative or a mixture of the trans- and cis-3-substituted-3-azabicyclo[3.2.1]octan-8-ol derivatives serving as a raw material is made available. However, it can be acquired by heating a 3-substituted-3-azabicyclo[3.2.1]octan-8-one derivative under reflux in a solvent, in the presence of an aluminum compound represented by the aforementioned formula $Al(OR^1)_3$ (in the formula, $R^1$ represents a hydrocarbon group in which a carbon atom having an oxygen atom bonded thereto is a secondary carbon atom), thereby conducting a reduction reaction. Here, as the aforementioned 3-substituted-3-azabicyclo[3.2.1]octan-8-one derivative, for example, a compound represented by the formula (3) shown below can be mentioned. Note that the 3-substituted-3-azabicyclo[3.2.1]octan-8-one derivative may have a substituent on the azabicyclo[3.2.1]octane ring, in a similar manner to that of the 3-substituted-3-azabicyclo[3.2.1]octan-8-ol derivatives represented by the aforementioned chemical formula (1) or (2), and examples of the substituent include the same substituents as those exemplified for the substituents of the 3-substituted-3-azabicyclo[3.2.1]octan-8-ol derivatives represented by the aforementioned chemical formula (1) or (2).

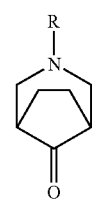

(3)

(In the formula, R is as defined above.)

The amount of aluminum compound added when conducting the aforementioned reduction reaction is typically within a range from 10 to 200 mol % and preferably within a range from 30 to 100 mol %, with respect to 1 mole of a 3-substituted-3-azabicyclo[3.2.1]octan-8-one derivative.

After obtaining a trans-3-substituted-3-azabicyclo[3.2.1]octan-8-ol derivative or a mixture of the trans- and cis-3-substituted-3-azabicyclo[3.2.1]octan-8-ol derivatives by the above method, it is preferable to remove a hydrogen donor compound, such as an alcohol, from the reaction solution by a method such as vacuum concentration.

There are no particular limitations on the solvent used in the present invention as long as it is a solvent other than an alcohol-based solvent or ketone-based solvent, and typical examples thereof include a hydrocarbon-based solvent, an ether-based solvent, a halogen-based solvent, and an aprotic polar solvent.

More specifically, hydrocarbon-based solvents such as n-hexane, cyclohexane, benzene, toluene, xylene, petroleum naphtha, solvent naphtha, petroleum ether, petroleum benzene, isoparaffin, normal paraffin, decalin, industrial gasoline, kerosene and ligroin; chlorofluorocarbon-based solvents such as $CBr_2ClCF_3$, $CClF_2CF_2CCl_3$, $CClF_2CF_2CHFCl$, $CF_3CF_2CHCl_2$, $CF_3CBrFCBrF_2$, $CClF_2CClFCF_2CCl_3$, $Cl(CF_2CFCl)_2Cl$, $Cl(CF_2CFCl)_2CF_2CCl_3$, and $Cl(CF_2CFCl)_3Cl$; fluorocarbon-based solvents such as Florinate (a product of 3M Company) and Aflude (a product of Asahi Glass Co. Ltd.); dichloroethylene, chlorobenzene, dichlorobenzene, dimethylformamide, dimethyl sulfoxide, N-methylpyrrolidone, ethyl acetate, butyl acetate, diethyl ether, dibutyl ether, tetrahydrofuran, dioxane, and the like can be mentioned.

As follows is a more detailed description of the present invention based on a series of examples, although the scope of the present invention is in no way limited by these examples.

EXAMPLE 1

10.8 g (50 mmol) of 3-benzyl-3-azabicyclo[3.2.1]octan-8-one (3') was dissolved in 50 ml of toluene, and 2.90 g (13.9 mmol) of aluminum isopropoxide was then added thereto, and the resulting mixture was heated to reflux for 2 hours under a nitrogen gas stream. Thereafter, 3.67 g (17.6 mmol) of aluminum isopropoxide was further added thereto, and the resulting mixture was heated to reflux for 30 minutes. 15 mL of a toluene solution containing 2.94 g (30 mmol) of cyclohexanone was then added thereto, and the resulting mixture was heated to reflux for 7 hours. The obtained reaction solution was analyzed by high performance liquid chromatography (hereafter, abbreviated as HPLC). As a result, it was observed that cis-3-benzyl-3-azabicyclo[3.2.1]octan-8-ol (1') was produced at a yield of 66.8%, whereas trans-3-benzyl-3-azabicyclo[3.2.1]octan-8-ol was produced at a yield of 17.4%.

EXAMPLE 2

186 mL of a toluene solution containing 25.35 g (0.12 mol) of aluminum isopropoxide was added to 40.2 g (0.19 mol) of trans-3-benzyl-3-azabicyclo[3.2.1]octan-8-ol (2'), and the resulting mixture was then heated to reflux for 30 minutes under a nitrogen gas stream. 23.6 g (0.24 mol) of cyclohexanone was then added thereto, and the resulting mixture was further heated to reflux for 13 hours.

After washing the obtained reaction solution twice with water, the organic layer thereof was concentrated, followed by a recrystallization using a mixed solution of toluene and hexane, thereby yielding 19.69 g of cis-3-benzyl-3-azabicyclo[3.2.1]octan-8-ol (1') at a yield of 45.3%.

EXAMPLE 3

Cyclohexanol (0.49 mol) was added to 200 mL of a toluene solution containing 34.4 g (0.16 mol) of aluminum isopropoxide, and 175 mL of isopropanol was removed by distillation at 95 to 98° C. 30 mL of a toluene solution containing 40.8 g (0.19 mol) of 3-benzyl-3-azabicyclo[3.2.1]octan-8-one (3') was then added thereto, and the resulting mixture was heated to reflux for 17 hours.

After washing the obtained reaction solution twice with 10% caustic soda, the organic layer thereof was concentrated, followed by a recrystallization using a mixed solution of toluene and hexane, thereby yielding 20.89 g of cis-3-benzyl-3-azabicyclo[3.2.1]octan-8-ol (1') at a yield of 47.3%.

EXAMPLE 4

4.2 g (20 mmol) of 3-benzyl-3-azabicyclo[3.2.1]octan-8-one (3') was dissolved in 10 ml of toluene, and 1.16 g (5.41 mmol) of aluminum isopropoxide was then added thereto, and the resulting mixture was heated to reflux for 3 hours under a nitrogen gas stream. Thereafter, 1.41 g (6.89 mmol) of aluminum isopropoxide was further added thereto, and the resulting mixture was heated to reflux for 30 minutes. 12.05 g (0.12 mol) of methyl isobutyl ketone (MIBK) was then added thereto, and the resulting mixture was heated to reflux for 9 hours. The obtained reaction solution was analyzed by high performance liquid chromatography. As a result, it was observed that cis-3-benzyl-3-azabicyclo[3.2.1]octan-8-ol (1') was produced at a yield of 59.3%, whereas trans-3-benzyl-3-azabicyclo[3.2.1]octan-8-ol (2') was produced at a yield of 14.2%.

INDUSTRIAL APPLICABILITY

According to the present invention, an isomerization from a trans-3-substituted-3-azabicyclo[3.2.1]octan-8-ol derivative to the cis form thereof can be achieved at a high yield, and thus it has become possible to provide a method which can be applied industrially.

The invention claimed is:
1. A method for producing a cis-3-substituted-3-azabicyclo[3.2.1]octan-8-ol derivative, the method comprising:
   conducting an isomerization of either a trans-3-substituted-3-azabicyclo[3.2.1]octan-8-ol derivative, or a mixture of the trans- and cis-3-substituted-3-azabicyclo [3.2.1]octan-8-ol derivatives,
   in the presence of an aluminum compound represented by a formula $Al(OR^1)_3$,
   wherein $R^1$ represents a hydrocarbon group in which a carbon atom having an oxygen atom bonded thereto is a secondary carbon atom; and
   a ketone compound represented by a formula $R^2$—CO—$R^3$,
   wherein $R^2$ and $R^3$ form a 5- to 10-membered ring together or $R^2$ and $R^3$ are different, and
   wherein $R^2$ and $R^3$ independently represent an alkyl group of 1 to 6 carbon atoms, a cycloalkyl group of 3 to 7 carbon atoms, an alkenyl group of 2 to 10 carbon atoms, a cycloalkenyl group of 4 to 10 carbon atoms, an aryl group of 6 to 10 carbon atoms, an aralkyl group of 7 to 10 carbon atoms, or a heterocyclic group formed of a 5- to 7-membered ring.

2. The method for producing a cis-3-substituted-3-azabicyclo[3.2.1]octan-8-ol derivative according to claim 1, wherein an $R^1$ group in the formula $Al(OR^1)_3$ represents a cycloalkyl group of 3 to 10 carbon atoms or a cycloalkenyl group of 4 to 10 carbon atoms.

3. The method for producing a cis-3-substituted-3-azabicyclo[3.2.1]octan-8-ol derivative according to claim 2, wherein the $R^1$ group represents a cycloalkyl group of 6 carbon atoms or a cycloalkenyl group of 6 carbon atoms.

4. The method for producing a cis-3-substituted-3-azabicyclo[3.2.1]octan-8-ol derivative according to claim 1, wherein $R^2$ and $R^3$ in the formula $R^2$—CO—$R^3$ form a 5- to 10-membered ring together.

5. The method for producing a cis-3-substituted-3-azabicyclo[3.2.1]octan-8-ol derivative according to claim 4, wherein $R^2$ and $R^3$ in the formula $R^2$—CO—$R^3$ form a 6-membered ring together.

6. The method for producing a cis-3-substituted-3-azabicyclo[3.2.1]octan-8-ol derivative according to claim 1, wherein either a trans-3-substituted-3-azabicyclo[3.2.1]octan-8-ol derivative or a mixture of the trans- and cis-3-substituted-3-azabicyclo[3.2.1]octan-8-ol derivatives is obtained by reducing a 3-substituted-3-azabicyclo[3.2.1]octan-8-one derivative.

7. A method for producing a cis-3-substituted-3-azabicyclo[3.2.1]octan-8-ol derivative, the method comprising:
   conducting a reaction for reducing a 3-substituted-3-azabicyclo[3.2.1]octan-8-one derivative, in the presence of trialkoxyaluminum in which a carbon atom having an oxygen atom bonded thereto is a secondary carbon atom, thereby obtaining either a trans-3-substituted-3-azabicyclo[3.2.1]octan-8-ol derivative, or a mixture of the trans- and cis-3-substituted-3-azabicyclo[3.2.1]octan-8-ol derivatives; and conducting an isomerization thereof,
   in the presence of an aluminum compound represented by a formula $Al(OR^1)_3$,
   wherein $R^1$ represents a hydrocarbon group in which a carbon atom having an oxygen atom bonded thereto is a secondary carbon atom; and
   a ketone compound represented by a formula $R^2$—CO—$R^3$,
   wherein $R^2$ and $R^3$ form a 5- to 10-membered ring together or $R^2$ and $R^3$ are different, and
   wherein $R^2$ and $R^3$ independently represent an alkyl group of 1 to 6 carbon atoms, a cycloalkyl group of 3 to 7 carbon atoms, an alkenyl group of 2 to 10 carbon atoms, a cycloalkenyl group of 4 to 10 carbon atoms, an aryl group of 6 to 10 carbon atoms, an aralkyl group of 7 to 10 carbon atoms, or a heterocyclic group formed of a 5- to 7-membered ring.

8. The method for producing a cis-3-substituted-3-azabicyclo[3.2.1]octan-8-ol derivative according to claim 2, wherein either a trans-3-substituted-3-azabicyclo[3.2.1]octan-8-ol derivative or a mixture of the trans- and cis-3-substituted-3-azabicyclo[3.2.1]octan-8-ol derivatives is obtained by reducing a 3-substituted-3-azabicyclo[3.2.1]octan-8-one derivative.

9. The method for producing a cis-3-substituted-3-azabicyclo[3.2.1]octan-8-ol derivative according to claim 3, wherein either a trans-3-substituted-3-azabicyclo[3.2.1]octan-8-ol derivative or a mixture of the trans- and cis-3-substituted-3-azabicyclo[3.2.1]octan-8-ol derivatives is obtained by reducing a 3-substituted-3-azabicyclo[3.2.1]octan-8-one derivative.

10. The method for producing a cis-3-substituted-3-azabicyclo[3.2.1]octan-8-ol derivative according to claim 4, wherein either a trans-3-substituted-3-azabicyclo[3.2.1]octan-8-ol derivative or a mixture of the trans- and cis-3-substituted-3-azabicyclo[3.2.1]octan-8-ol derivatives is obtained by reducing a 3-substituted-3-azabicyclo[3.2.1]octan-8-one derivative.

11. The method for producing a cis-3-substituted-3-azabicyclo[3.2.1]octan-8-ol derivative according to claim 5, wherein either a trans-3-substituted-3-azabicyclo[3.2.1]octan-8-ol derivative or a mixture of the trans- and cis-3-substituted-3-azabicyclo[3.2.1]octan-8-ol derivatives is obtained by reducing a 3-substituted-3-azabicyclo[3.2.1]octan-8-one derivative.

* * * * *

UNITED STATES PATENT AND TRADEMARK OFFICE
CERTIFICATE OF CORRECTION

| | | |
|---|---|---|
| PATENT NO. | : 8,461,340 B2 | Page 1 of 1 |
| APPLICATION NO. | : 12/674326 | |
| DATED | : June 11, 2013 | |
| INVENTOR(S) | : Hakuta et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 398 days.

Signed and Sealed this
Sixth Day of January, 2015

Michelle K. Lee
*Deputy Director of the United States Patent and Trademark Office*